US011103185B2

(12) United States Patent
Denda

(10) Patent No.: US 11,103,185 B2
(45) Date of Patent: Aug. 31, 2021

(54) SENSOR MODULE

(71) Applicant: SHINKO ELECTRIC INDUSTRIES CO., LTD., Nagano (JP)

(72) Inventor: Tatsuaki Denda, Nagano (JP)

(73) Assignee: SHINKO ELECTRIC INDUSTRIES CO., LTD., Nagano (JP)

( * ) Notice: Subject to any disclaimer, the term of this patent is extended or adjusted under 35 U.S.C. 154(b) by 49 days.

(21) Appl. No.: 16/541,558

(22) Filed: Aug. 15, 2019

(65) Prior Publication Data

US 2020/0054281 A1 Feb. 20, 2020

(30) Foreign Application Priority Data

Aug. 20, 2018 (JP) .............................. JP2018-154134

(51) Int. Cl.
*A61B 5/1455* (2006.01)
*A61B 5/00* (2006.01)
(Continued)

(52) U.S. Cl.
CPC ............ *A61B 5/6826* (2013.01); *A61B 5/002* (2013.01); *A61B 5/02141* (2013.01);
(Continued)

(58) Field of Classification Search
CPC .. H01Q 1/273; H01Q 1/2283; H01L 2924/00; H01L 2223/6677; H01L 2924/00014;
(Continued)

(56) References Cited

U.S. PATENT DOCUMENTS 5,676,139 A * 10/1997 Goldberger ........ A61B 5/02444
356/41
5,810,724 A * 9/1998 Gronvall ............ A61B 5/02427
600/310

(Continued)

FOREIGN PATENT DOCUMENTS

JP 2007-105316 4/2007

OTHER PUBLICATIONS

Billah S.M. (2018) Dielectric Polymers. In: Jafar Mazumder M., Sheardown H., Al-Ahmed A. (eds) Functional Polymers. Polymers and Polymeric Composites: A Reference Series. Springer, Cham, https://doi.org/10.1007/978-3-319-92067-2_8-1 (Year: 2018).*

*Primary Examiner* — Patrick Fernandes
*Assistant Examiner* — Liam A Wallace
(74) *Attorney, Agent, or Firm* — Rankin, Hill & Clark LLP

(57) ABSTRACT

A semiconductor device includes an antenna mounted on a wiring substrate. A holding member includes a first plate-shaped part having a first surface and a second surface, a second plate-shaped part having a third surface and a fourth surface, and a coupling part configured to couple the first plate-shaped part and the second plate-shaped part so that the second surface and the third surface have parts facing each other with a space therebetween. The one end of the wiring substrate is fixed to the holding member so that the antenna overlaps the coupling part, as seen from above. A part continuing to the one end of the wiring substrate is folded back so as to being arranged sequentially along the first surface, the second surface, the third surface, and the fourth surface. The other end of the wiring substrate extends in an elastically deformable state from the fourth surface.

10 Claims, 10 Drawing Sheets

(51) Int. Cl.
  *H01Q 1/27* (2006.01)
  *H01Q 1/22* (2006.01)
  *H05K 1/18* (2006.01)
  *A61B 5/021* (2006.01)
  *A61B 5/024* (2006.01)

(52) U.S. Cl.
  CPC ...... *A61B 5/02427* (2013.01); *A61B 5/02433* (2013.01); *A61B 5/1455* (2013.01); *A61B 5/14552* (2013.01); *H01Q 1/2283* (2013.01); *H01Q 1/273* (2013.01); *H05K 1/189* (2013.01); *A61B 2560/0214* (2013.01); *A61B 2562/0233* (2013.01); *A61B 2562/227* (2013.01); *H01L 2223/6677* (2013.01); *H01L 2924/00* (2013.01); *H01L 2924/00014* (2013.01); *H05K 2201/055* (2013.01); *H05K 2201/056* (2013.01); *H05K 2201/10106* (2013.01); *H05K 2201/10151* (2013.01); *H05K 2201/10189* (2013.01); *Y10T 29/4913* (2015.01)

(58) Field of Classification Search
  CPC .......... G01L 2224/48091; H05K 1/189; H05K 2201/055; H05K 2201/056; H05K 2201/10106; H05K 2201/10151; H05K 2201/10189; Y10T 29/4913; A61B 5/6826; A61B 5/002; A61B 5/02427; A61B 5/02433; A61B 5/1455; A61B 5/14552; A61B 2560/0214; A61B 2562/277; A61B 2562/0233
  See application file for complete search history.

(56) References Cited

U.S. PATENT DOCUMENTS

| | | | |
|---|---|---|---|
| 9,717,458 B2* | 8/2017 | Lamego | A61B 5/14551 |
| 2007/0123756 A1 | 5/2007 | Kitajima et al. | |
| 2016/0151008 A1* | 6/2016 | Tateda | A61B 5/02416 600/476 |
| 2016/0209920 A1* | 7/2016 | Mastandrea | G06F 3/03547 |

* cited by examiner

SENSOR MODULE

CROSS-REFERENCE TO RELATED APPLICATIONS

This application is based upon and claims the benefit of priority from prior Japanese patent application No. 2018-154134, filed on Aug. 20, 2018, the entire contents of which are incorporated herein by reference.

TECHNICAL FIELD

The present disclosure relates to a sensor module.

BACKGROUND ART

A variety of sensor modules configured to detect a variety of biometric information from a human body have been developed. As the sensor module, a pulse oximeter may be exemplified which is configured to mount a probe, which includes a light-emitting unit and a light-receiving unit, to a finger of a test subject, to emit light toward the finger, to measure a change in amount of the light having passed through the finger, and to measure a blood oxygen saturation level with a control circuit including a CPU. A measurement result of the blood oxygen saturation level is displayed on a display unit mounted on the sensor module.

CITATION LIST

Patent Literature

[PTL 1]
JP-A-2007-105316

SUMMARY OF INVENTION

However, according to the sensor module, while it is possible to check the measurement result of the blood oxygen saturation level on the display unit, it is not possible to transmit the measurement result to an outside, as data. For example, it is considered to mount an antenna to the sensor module for wireless transmission of data. However, a dielectric constant of the finger is high, such as 40 to 70, and is different depending on persons. Therefore, even when the antenna is simply mounted on the sensor module, the antenna is influenced by the electric constant of the finger, so that it is difficult to implement stable communication performance.

Aspect of non-limiting embodiments of the present disclosure is to provide a sensor module capable of implementing stable wireless communication performance.

Aspects of certain non-limiting embodiments of the present disclosure address the features discussed above and/or other features not described above. However, aspects of the non-limiting embodiments are not required to address the above features, and aspects of the non-limiting embodiments of the present disclosure may not address features described above.

According to an aspect of the present disclosure, there is provided a sensor module comprising:

a semiconductor device comprising a flexible wiring substrate and a plurality of electronic components mounted on the wiring substrate, the electronic components including an antenna, the antenna being mounted on the wiring substrate at one end of the wiring substrate; and a holding member configured to hold a part of the semiconductor device, the holding member comprises:

a first plate-shaped part having a first surface and a second surface, the second surface being an opposite surface to the first surface, a second plate-shaped part having a third surface and a fourth surface, the fourth surface being an opposite surface to the third surface, and a coupling part configured to couple the first plate-shaped part and the second plate-shaped part each other so that the second surface and the third surface have parts facing each other with a space therebetween, wherein the one end of the wiring substrate is fixed to the holding member so that the antenna overlaps the coupling part, as seen from above, and the antenna does not overlap the other electronic components, as seen from above, wherein a part continuing to the one end of the wiring substrate is folded back so as to being arranged sequentially along the first surface, the second surface, the third surface, and the fourth surface, and wherein the other end of the wiring substrate extends in an elastically deformable state from the fourth surface.

According to the present disclosure, it is possible to provide the sensor module capable of implementing stable wireless communication performance.

BRIEF DESCRIPTION OF DRAWINGS

Exemplary embodiment(s) of the present disclosure will be described in detail based on the following figures, wherein.

DESCRIPTION OF EMBODIMENTS

Figure 1:
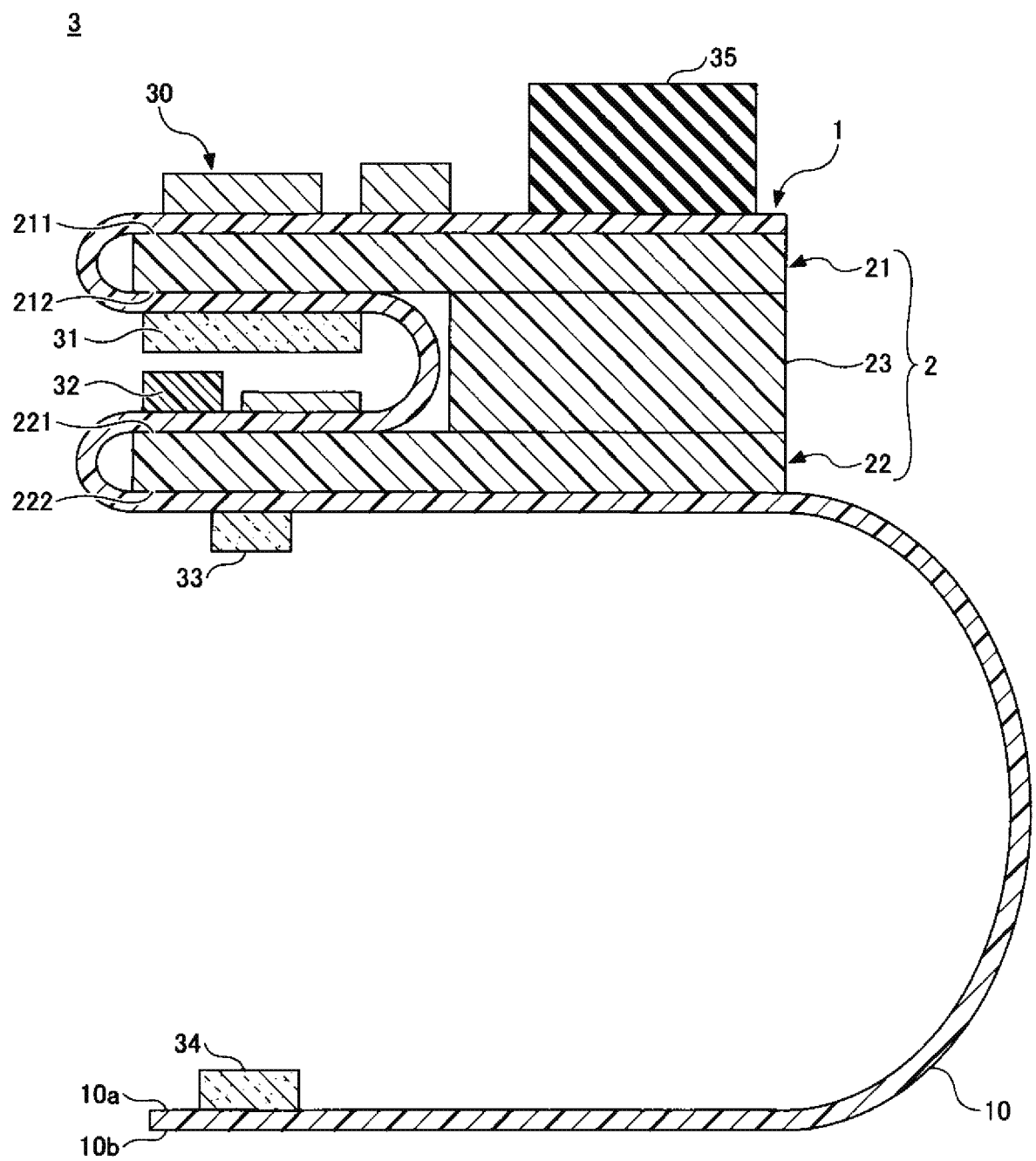
FIG. 1 is a sectional view exemplifying a sensor module in accordance with a first exemplary embodiment.

Hereinafter, exemplary embodiments will be described in detail with reference to the drawings. In the respective drawings, the same configurations are denoted with the same reference numerals, and the overlapping descriptions thereof may be omitted.

First Exemplary Embodiment

FIG. 1 is a sectional view exemplifying a sensor module in accordance with a first exemplary embodiment. As shown in FIG. 1, a sensor module 3 includes a semiconductor device 1, and a holding member 2. In the below, the semiconductor device 1, the holding member 2 and the sensor module 3 are sequentially described.

Figure 2A:
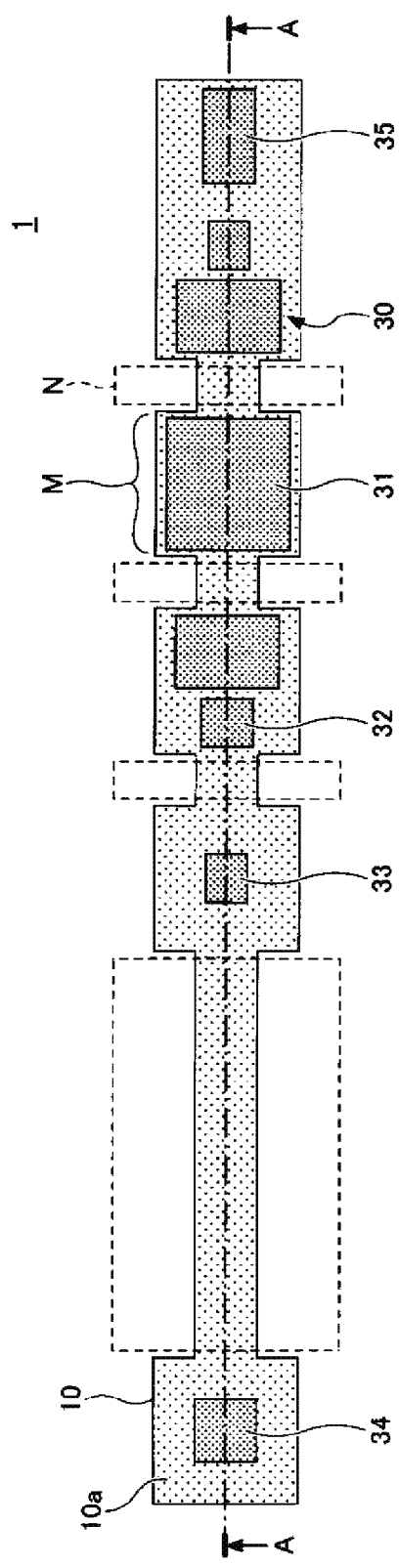
FIGS. 2A and 2B are views exemplifying a semiconductor device in accordance with the first exemplary embodiment.
Figure 2B:
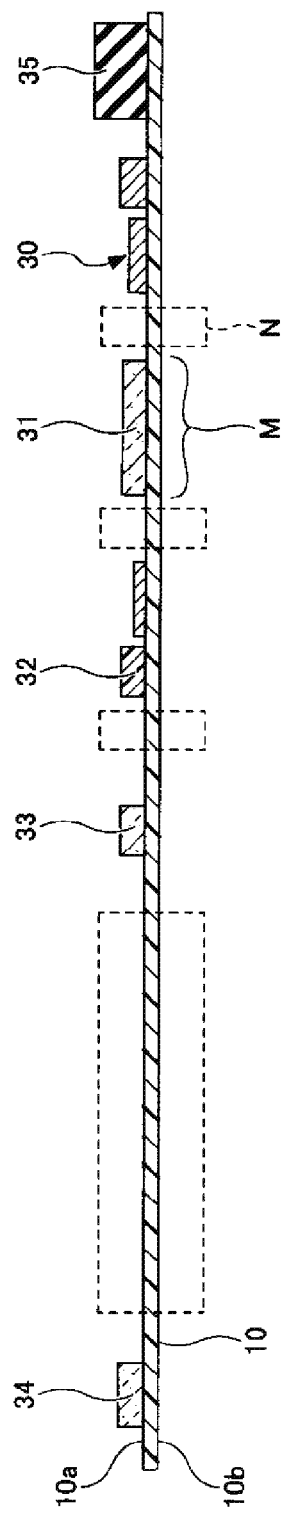

(Semiconductor Device) FIGS. 2A and 2B are views exemplifying the semiconductor device in accordance with the first exemplary embodiment, in which FIG. 2A is a plan view, and FIG. 2B is a sectional view taken along a line A-A of FIG. 2A. FIGS. 2A and 2B depict a state before the semiconductor device 1 is assembled (bent) as a part of the sensor module 3. Referring to FIGS. 2A and 2B, the semiconductor device 1 includes a wiring substrate 10, and electronic components 30.

Figure 3:
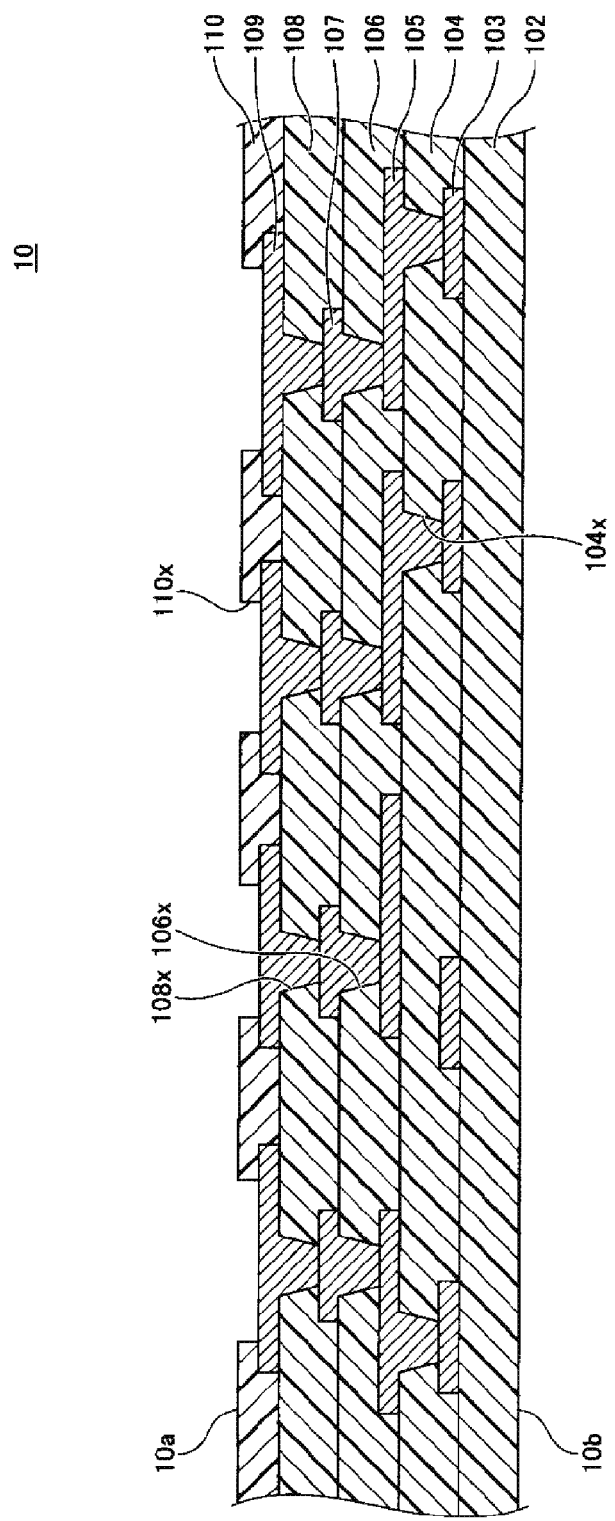
FIG. 3 is a sectional view exemplifying a wiring substrate of the semiconductor device in accordance with the first exemplary embodiment.

The wiring substrate 10 is a flexible coreless substrate, and has a multi-layered structure (for example, four layers) where a plurality of wiring layers is stacked via insulating layers, as shown in FIG. 3. Here, the flexibility indicates a property allowing bending and flexing. The wiring substrate 10 can be manufactured by a well-known buildup method, for example.

In the example of FIG. 3, the wiring substrate 10 has a structure where an insulating layer 102, a wiring layer 103, an insulating layer 104, a wiring layer 105, an insulating layer 106, a wiring layer 107, an insulating layer 108, a wiring layer 109, and a solder resist layer 110 are sequentially stacked. However, the numbers of the wiring layers and the insulating layer to be stacked may be appropriately determined, as required.

In the meantime, in the first exemplary embodiment, for convenience sake, the solder resist layer 110-side of the wiring substrate 10 is referred to as 'upper side' or 'one side', and the insulating layer 102-side is referred to as 'lower side' or 'the other side'. Also, a surface of each part facing toward the solder resist layer 110 is referred to as 'one surface' or 'upper surface', and a surface facing toward the insulating layer 102 is referred to as 'the other surface' or 'lower surface'. However, the wiring substrate 10 can be used upside down or can be arranged at any angle. Also, the description 'as seen from above' indicates that a target is seen from a normal direction of one surface 10a of the wiring substrate 10 (an upper surface of the solder resist layer 110), and the planar shape indicates a shape of the target, as seen from the normal direction of one surface 10a of the wiring substrate 10 (the upper surface of the solder resist layer 110).

The insulating layer 102 is an insulating layer becoming one outermost layer. As a material of the insulating layer 102, a flexible insulating resin (for example, a thermosetting resin) having a low Young's modulus may be used, for example. As the flexible insulating resin having a low Young's modulus, for example, an insulating resin of which a main component is a polyimide-based resin, an epoxy-based resin or the like may be exemplified. A thickness of the insulating layer 102 may be set to about 20 μm to 45 μm, for example. The insulating layer 102 may contain filler such as silica ($SiO_2$).

The wiring layer 103 is formed on one surface of the insulating layer 102. As a material of the wiring layer 103, for example, copper (Cu) and the like may be exemplified. A thickness of the wiring layer 103 may be set to about 10 μm to 20 μm, for example. The wiring layer 103 may be formed as a fine wiring of which line and space (hereinafter, referred to as 'line/space') are about 10 μm/10 μm to 20 μm/20 μm. In the meantime, the line of the line/space indicates a wiring width, and the space indicates an interval between the adjacent wirings (wiring interval). For example, the line/space of 10 μm/10 μm indicates that the wiring width is 10 μm and the interval between the adjacent wirings is 10 μm.

The insulating layer 104 is formed on one surface of the insulating layer 102 so as to cover the wiring layer 103. A material and a thickness of the insulating layer 104 may be the same as the insulating layer 102, for example. The insulating layer 104 may contain filler such as silica ($SiO_2$).

The wiring layer 105 is formed on one side of the insulating layer 104, and is electrically connected to the wiring layer 103. The wiring layer 105 includes via wirings filled in via holes 104x penetrating the insulating layer 104 and formed to expose one surface of the wiring layer 103, and a wiring pattern formed on one surface of the insulating layer 104. The via hole 104x may be formed as a concave portion having an inverted conical shape where a diameter of an opening opened toward the insulating layer 106 is larger than a diameter of a bottom surface of an opening formed by the upper surface of the wiring layer 103. The diameter of the opening of the via hole 104x may be set to about 60 μm to 70 μm, for example. A material of the wiring layer 105, and a thickness and a line/space of the wiring pattern of the wiring layer 105 may be the same as the wiring layer 103, for example.

The insulating layer 106 is formed on one surface of the insulating layer 104 so as to cover the wiring layer 105. A material and a thickness of the insulating layer 106 may be the same as the insulating layer 102, for example. The insulating layer 106 may contain filler such as silica ($SiO_2$).

The wiring layer 107 is formed on one side of the insulating layer 106, and is electrically connected to the wiring layer 105. The wiring layer 107 includes via wirings filled in via holes 106x penetrating the insulating layer 106 and formed to expose one surface of the wiring layer 105, and a wiring pattern formed on one surface of the insulating layer 106. The via hole 106x may be formed as a concave portion having an inverted conical shape where a diameter of an opening opened toward the insulating layer 108 is larger than a diameter of a bottom surface of an opening formed by the upper surface of the wiring layer 105. The diameter of the opening of the via hole 106x may be set to about 60 μm to 70 μm, for example. A material of the wiring layer 107, and a thickness and a line/space of the wiring pattern of the wiring layer 107 may be the same as the wiring layer 103, for example.

The insulating layer 108 is formed on one surface of the insulating layer 106 so as to cover the wiring layer 107. A material and a thickness of the insulating layer 108 may be the same as the insulating layer 102, for example. The insulating layer 108 may contain filler such as silica ($SiO_2$).

The wiring layer 109 is formed on one side of the insulating layer 108, and is electrically connected to the wiring layer 107. The wiring layer 109 includes via wirings filled in via holes 108x penetrating the insulating layer 108 and formed to expose one surface of the wiring layer 107, and a wiring pattern formed on one surface of the insulating layer 108. The via hole 108x may be formed as a concave portion having an inverted conical shape where a diameter of an opening opened toward the solder resist layer 110 is larger than a diameter of a bottom surface of an opening formed by the upper surface of the wiring layer 107. The diameter of the opening of the via hole 108x may be set to about 60 μm to 70 μm, for example. A material of the wiring layer 109, and a thickness and a line/space of the wiring pattern of the wiring layer 109 may be the same as the wiring layer 103, for example.

The solder resist layer 110 is an insulating layer becoming the other outermost layer. The solder resist layer 110 is formed on one surface of the insulating layer 108 so as to cover the wiring layer 109. The solder resist layer 110 may be formed of a photosensitive resin such as an epoxy-based resin, an acryl-based resin and the like, for example. A thickness of the solder resist layer 110 may be set to about 15 μm to 35 μm, for example.

The solder resist layer 110 has openings 110x, and portions of the upper surface of the wiring layer 109 are exposed in the openings 110x. A planar shape of the opening 110x may be circular, for example. If necessary, the upper surface of the wiring layer 109 exposed in the openings 110x may be formed with a metal layer or may be subjected to antioxidant processing such as OSP (Organic Solderability Preservative) processing. As the metal layer, an Au layer, a Ni/Au layer (a metal layer having a Ni layer and an Au layer stacked in corresponding order), a Ni/Pd/Au layer (a metal layer having a Ni layer, a Pd layer and an Au layer stacked in corresponding order), and the like may be exemplified.

The wiring layer 109 exposed in the openings 110x may be used as pads that are to be connected to terminals of electronic components or pads for checking a signal waveform. Meanwhile, a wiring layer to be covered to the lowest insulating layer 102 may be provided, as required. In this case, for example, a lower surface of the wiring layer may be exposed from the lower surface of the insulating layer. Thereby, the electronic components 30 can be mounted on the other surface 10b of the wiring substrate 10, too.

Returning to FIGS. 2A and 2B, one surface 10a of the wiring substrate 10 (the upper surface of the solder resist layer 110) is mounted thereon with a plurality of electronic components 30.

The electronic components 30 include a semiconductor component and a passive component. As the semiconductor component, for example, a CPU (Central Processing Unit), a ROM (Read Only Memory), a RAM (Random Access Memory), an LED (Light-Emitting Diode), a PD (Photo Diode) and the like may be exemplified. As the passive component, for example, a resistance, a capacitor, an inductor, an antenna, a connector and the like may be exemplified.

The main components of the electronic components 30 are described with the reference numerals denoted thereto. The semiconductor device 1 includes, for example, a CPU 31, a connector 32, an LED 33, a PD 34, and an antenna 35, and has a function of acquiring predetermined information from a measurement target. The CPU 31 is configured to control the entire semiconductor device 1. The CPU 31 is an electronic component, which has the largest area, as seen from above, of the electronic components 30 mounted on the semiconductor device 1. The connector 32 is a terminal to which power to be supplied to the CPU 31 and the like is to be input from an outside. The LED 33 is a light-emitting element configured to emit light of a predetermined wavelength region (for example, red light or infrared light) to the measurement target under control of the CPU 31. The PD 34 is a light-receiving element configured to receive reflected light or transmitted light from the measurement target with respect to the emitted light from the LED 33, to convert the same into an electric signal and to transmit the electric signal to the CPU 31. The antenna 35 is an electronic component configured to transmit and receive a radio wave between the semiconductor device 1 and an outside. The antenna 35 is mounted on one surface 10a of the wiring substrate 10 at one end of the wiring substrate 10. In other words, the antenna 35 is mounted on the one surface 10a of the wiring substrate 10 at one end-side of the semiconductor device 1.

In the example of FIGS. 2A and 2B, all the electronic components 30 including the CPU 31, the connector 32, the LED 33, the PD 34 and the antenna 35 are mounted on one surface 10a of the wiring substrate 10 but may be mounted on the other surface 10b of the wiring substrate 10, as required.

In the semiconductor device 1, component mounting parts M in which the electronic components 30 are mounted on the wiring substrate 10 and component non-mounting parts N (regions surrounded by the broken lines in FIGS. 2A and 2B) in which the electronic component 30 is not mounted on the wiring substrate 10 are alternately arranged in a longitudinal direction of the semiconductor device 1.

The semiconductor device 1 is designed with the assumption that it is to be used with being bent at a plurality of places in the longitudinal direction. In the semiconductor device 1, the component mounting parts M and the component non-mounting parts N are alternately arranged, so that the semiconductor device 1 can be easily deformed by bending the respective component non-mounting parts N.

Also, a width of the component non-mounting part N is set narrower than a width of the component mounting part M, so that it is possible to further easily bend the component non-mounting part N. However, the width of the component non-mounting part N may be set to be the same as the width of the component mounting part M, depending on the required specification.

In the meantime, the wiring pattern of each wiring layer may be arranged in any of the component mounting part M and the component non-mounting part N. However, the via wiring is preferably arranged only in the component mounting part M. The via wiring is arranged only in the component mounting part M, which is not bent at all or is little bent, so that it is possible to prevent the via wiring from being cracked when bending the component non-mounting part N.

(Holding Member)

Figure 4:
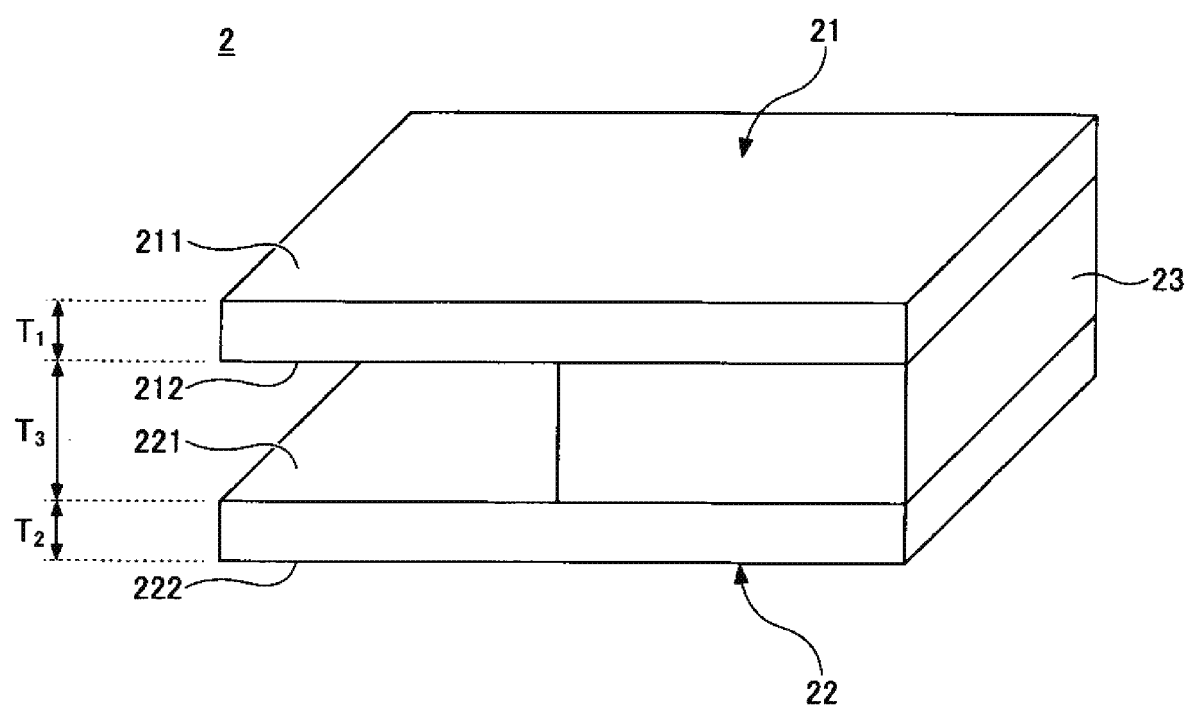
FIG. 4 is a perspective view exemplifying a holding member in accordance with the first exemplary embodiment.

FIG. 4 is a perspective view exemplifying the holding member in accordance with the first exemplary embodiment. Referring to FIG. 4, the holding member 2 includes a first plate-shaped part 21, a second plate-shaped part 22, and a coupling part 23, and can hold a part of the semiconductor device 1. The holding member 2 may be formed into a U-shape, for example, as seen from a side, by the first plate-shaped part 21, the second plate-shaped part 22, and the coupling part 23.

The first plate-shaped part 21 has a first surface 211 and a second surface 212 that is an opposite surface to the first surface 211. The second plate-shaped part 22 has a third surface 221 and a fourth surface 222 that is an opposite surface to the third surface 221. The planar shapes of the first plate-shaped part 21 and the second plate-shaped part 22 may be rectangular, for example.

The coupling part 23 is configured to couple the first plate-shaped part 21 and the second plate-shaped part 22 each other so that the second surface 212 of the first plate-shaped part 21 and the third surface 221 of the second plate-shaped part 22 have parts facing each other with a space therebetween. The space formed by the second surface 212 of the first plate-shaped part 21 and the third surface 221 of the second plate-shaped part 22 becomes a space in which a part of the semiconductor device 1 is accommodated with being bent.

A thickness of each part of the holding member 2 may be appropriately determined, as required. For example, a thickness $T_1$ of the first plate-shaped part 21 may be set to about 1 mm, a thickness $T_2$ of the second plate-shaped part 22 may be set to about 1 mm, and a thickness $T_3$ of the coupling part 23 (an interval between the first plate-shaped part 21 and the second plate-shaped part 22) may be set to about 2 mm. In this case, an entire thickness of the holding member 2 is about 4 mm.

As described later, a region, in which the antenna 35 is mounted, of the semiconductor device 1 is fixed on the coupling part 23 of the holding member 2. In other words, the one end of the wiring substrate 10 on which the antenna 35 is mounted is fixed on the coupling part 23 of the holding member 2. Since the antenna 35 is likely to be influenced by a dielectric constant of an adjacent material, a material having dielectric constant ranging from 1 to 5 is preferably used as the first plate-shaped part 21, the second plate-shaped part 22 and the coupling part 23 so that the antenna 35 is to exhibit stable communication performance. As the material having the dielectric constant ranging from 1 to 5, acryl having a dielectric constant ranging from 2.7 to 4.5 may be exemplified.

Also, as the material having the dielectric constant ranging from 1 to 5, ABS resin having a dielectric constant ranging from 2.4 to 4.1, silicone resin having a dielectric constant ranging from 3.5 to 5.0, polycarbonate resin having a dielectric constant ranging from 2.9 to 3.0, polyacetal resin having a dielectric constant ranging from 3.6 to 3.7, polypropylene resin having a dielectric constant ranging from 2.0 to 2.3, and polyethylene terephthalate resin having a dielectric constant ranging from 2.9 to 3.0 may be exemplified.

When acryl is used for the first plate-shaped part 21, the second plate-shaped part 22 and the coupling part 23, the first plate-shaped part 21 and the coupling part 23, and the second plate-shaped part 22 and the coupling part 23 are respectively bonded using an acryl-based adhesive. Thereby, the dielectric constant of the holding member 2 including the adhesive may be set to 1 to 5. In the meantime, for example, a cuboid-shaped acryl may be cut to manufacture the holding member 2 having the first plate-shaped part 21, the second plate-shaped part 22, and the coupling part 23. In this case, it is possible to implement the holding member 2 made of acryl without using an adhesive. In the meantime, acryl is favorable because it can be easily processed and is inexpensive.

(Sensor Module)

Returning to FIG. 1, in the sensor module 3, one end-side of the semiconductor device 1 (a side on which the antenna 35 is mounted) is fixed to the holding member 2 so that the antenna 35 is to overlap the coupling part 23 of the holding member 2, as seen from above, and the antenna 35 does not overlap the other electronic components 30, as seen from above.

A part continuing to one end-side of the semiconductor device 1 is folded back so as to sequentially contact the first surface 211 of the first plate-shaped part 21, the second surface 212 of the first plate-shaped part 21, the third surface 221 of the second plate-shaped part 22 and the fourth surface 222 of the second plate-shaped part 22. Specifically, the semiconductor device 1 is folded back by about 180° at a part ranging from the first surface 211 of the first plate-shaped part 21 to the second surface 212 of the first plate-shaped part 21. Also, the semiconductor device 1 is folded back by about 180° at a part ranging from the second surface 212 of the first plate-shaped part 21 to the third surface 221 of the second plate-shaped part 22. Also, the semiconductor device 1 is folded back by about 180° at a part ranging from the third surface 221 of the second plate-shaped part 22 to the fourth surface 222 of the second plate-shaped part 22. The part continuing to the one end-side of the semiconductor device 1 may be folded back so as to being arranged sequentially along the first surface 211, the second surface 212, the third surface, 221 and the fourth surface 222.

The other end-side of the semiconductor device 1 extends in an elastically deformable state from the coupling part 23-side of the fourth surface 222 of the second plate-shaped part 22. That is, a region, which extends from the fourth surface 222 of the second plate-shaped part 22, of the semiconductor device 1 can be freely flexed or curved. In the meantime, a flexed or curved part and a flexible or curvable of the semiconductor device 1 are the component non-mounting parts N.

Meanwhile, in FIG. 1, the region extending from the fourth surface 222 of the second plate-shaped part 22 is shown with being curved. However, this is just exemplary. As described above, the region extending from the fourth surface 222 of the second plate-shaped part 22 can be freely flexed or curved.

Here, a specific using method of the sensor module 3 is described in an example where the sensor module 3 is configured as a wearable device for measuring an arterial blood oxygen saturation ($SPO_2$). However, this is just exemplary, and the sensor module 3 may be used to measure a target other than the arterial blood oxygen saturation. As the measurement target other than the arterial blood oxygen saturation, a pulse and a blood pressure may be exemplified.

Figure 5:
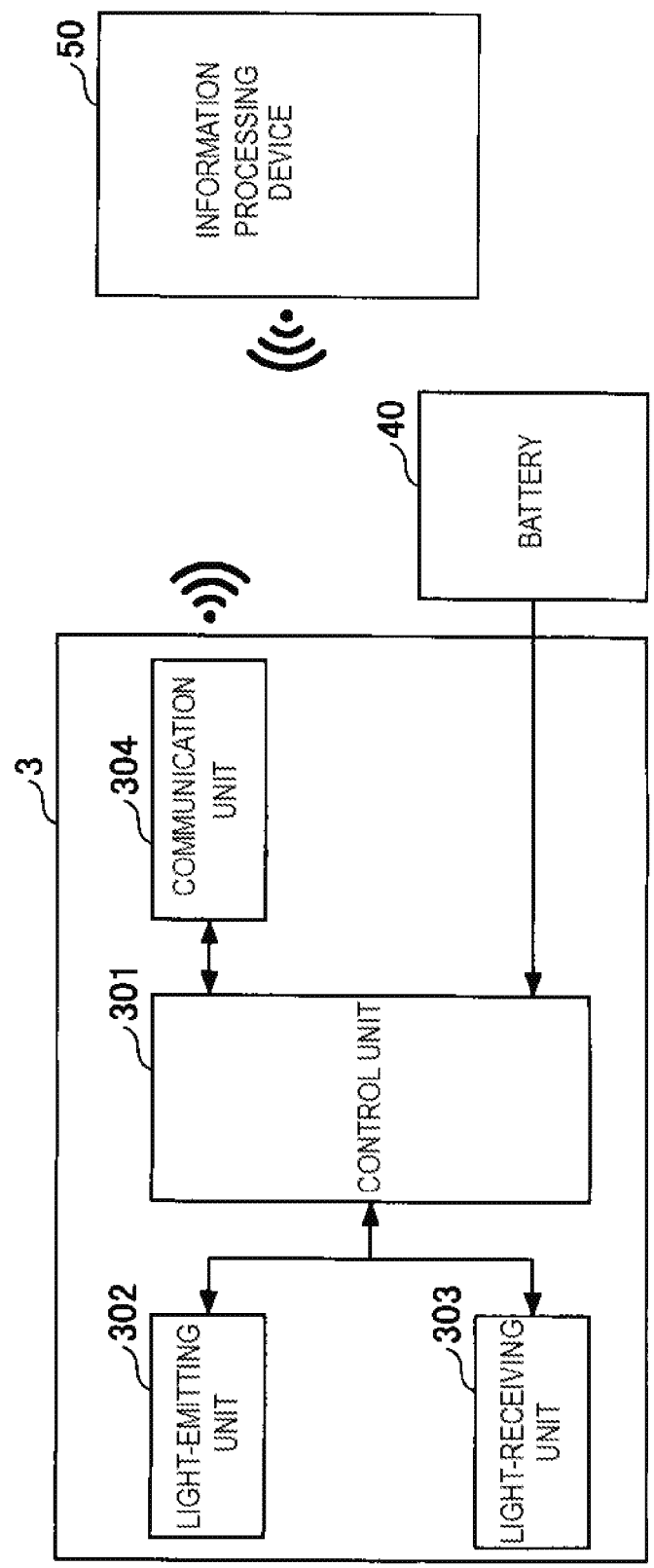
FIG. 5 is a view exemplifying functional blocks of the sensor module in accordance with the first exemplary embodiment.

FIG. 5 is a view exemplifying functional blocks of the sensor module in accordance with the first exemplary embodiment. As shown in FIG. 5, the sensor module 3 has, as functional blocks, a control unit 301, a light-emitting unit 302, a light-receiving unit 303, and a communication unit 304. The sensor module 3 may have other functional blocks, as required.

The control unit 301 may include, for example, the CPU 31, a ROM, a RAM, a main memory and the like. In this case, a program stored in the ROM is read into the main memory and is executed by the CPU 31, so that a variety of functions of the control unit 301 may be implemented. In the meantime, the control unit 301 may be implemented only by hardware. The control unit 301 may be operated by power supplied from a battery 40 arranged outside the sensor module 3.

The light-emitting unit 302 has a function of emitting infrared light or red light under control of the control unit 301. The light-emitting unit 302 may be implemented by an LED 33 in which an IR LED, which is a light-emitting diode configured to emit infrared light, and a RED LED, which is a light-emitting diode configured to emit red light, are configured as one chip, for example.

The light-receiving unit 303 has functions of receiving transmitted light of light irradiated from the light-emitting unit 302 to the measurement target and converting the received light into an electric signal. The light-receiving unit 303 may be implemented by the PD 34, for example. The information obtained as a result of the conversion of the received light into the electric signal by the light-receiving unit 303 is transmitted to the CPU 31.

The communication unit 304 has a function of wirelessly transmitting and receiving the information between the control unit 301 and an information processing device 50 arranged outside the sensor module 3. The information processing device 50 is, for example, a personal computer or a tablet terminal. The communication unit 304 may be implemented by a communication device (not shown) and the antenna 35, for example. The communication unit 304 can transmit data of $SPO_2$, which is calculated on the basis of an output of the light-receiving unit 303 by the control unit 301, to the information processing device 50, for example.

Here, a measurement principle of $SPO_2$ is described. $SPO_2$ is a value indicating a percentage of hemoglobin, which is combined with oxygen, of hemoglobin contained in erythrocytes flowing in the blood (arterial blood) being transported from the heart to the whole body. When hemoglobin is combined with oxygen, hemoglobin exhibits red group colors. On the other hand, when hemoglobin is not combined with oxygen, hemoglobin exhibits black group colors. This shows that when hemoglobin is combined with oxygen, red light can easily penetrate therethrough, and when hemoglobin is not combined with oxygen, the entire visible light including red light is difficult to penetrate therethrough. On the other hand, the infrared light can easily penetrate, irrespective of whether hemoglobin is combined with oxygen.

Therefore, when the red light is irradiated to a fingertip from the RED LED, which is the light-emitting unit 302, if hemoglobin and oxygen are much combined, a ratio of the red light to be transmitted increases, so that an amount of the red light to be received by the light-receiving unit 303 increases. In contrast, if hemoglobin and oxygen are less combined, the ratio of the red light to be transmitted decreases, so that the amount of the red light to be received by the light-receiving unit 303 decreases.

On the other hand, when the fingertip is irradiated with the infrared light from the RED LED, which is the light-emitting unit 302, a ratio of the infrared light to be transmitted increases, irrespective of whether hemoglobin and oxygen are much combined, so that the amount of the infrared light to be received by the light-receiving unit 303 always increases.

That is, it is possible to measure $SPO_2$ by calculating a ratio of the amount of the red light, which is to be received by the light-receiving unit 303 when the red light is irradiated, and the amount of the infrared light, which is to be received by the light-receiving unit 303 when the infrared light is irradiated. For example, the control unit 301 can calculate $SPO_2$ on the basis of the ratio of the amount of the red light and the amount of the infrared light.

Figure 6:
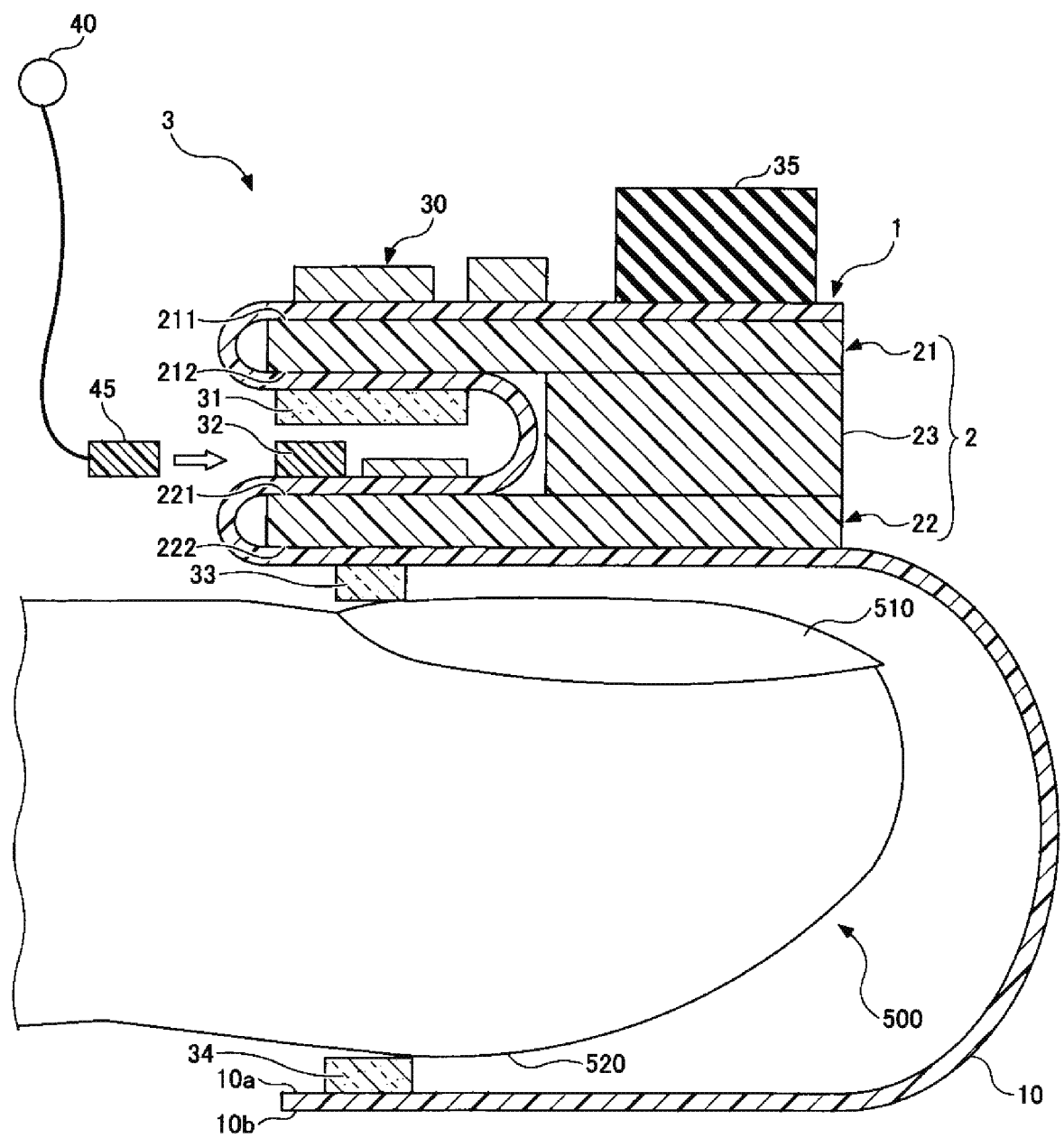
FIG. 6 is a sectional view illustrating a using method of the sensor module in accordance with the first exemplary embodiment.

FIG. 6 is a sectional view illustrating a using method of the sensor module in accordance with the first exemplary embodiment, and depicts a state where the sensor module 3 is mounted on a fingertip 500 of a test subject who is a measurement target.

In the semiconductor device 1 of the sensor module 3, one of the LED 33 and the PD 34 is mounted in a region arranged in the fourth surface 222 of the second plate-shaped part 22, and the other of the LED 33 and the PD 34 is mounted in a region extending from the fourth surface 222. In the first exemplary embodiment, for example, the LED 33 is mounted in the region arranged in the fourth surface 222 of the second plate-shaped part 22, and the PD 34 is mounted in the region extending from the fourth surface 222.

The sensor module 3 can be mounted to the fingertip 500 of the test subject by arranging the holding member 2 at a nail 510-side of the fingertip 500 of the test subject and inflecting the region extending from the fourth surface 222 from the nail 510-side of the fingertip 500 of the test subject toward a bulging part 520-side. In this case, the LED 33 and the PD 34 may be arranged to face each other with the fingertip 500 being interposed therebetween. Thereby, the light emitted from the LED 33 can penetrate the fingertip 500 and can be then received at the PD 34. In the meantime, the sensor module 3 may be accommodated in a housing made of silicone so as to easily mount the same to the fingertip 500 and to protect semiconductor device 1.

The connector 32 of the sensor module 3 is fitted with a connector 45 connected to the battery 40 by a wire rod or the like, for example. The battery 40 is, for example, a button-type battery, and may be mounted on a wrist or the like. In the meantime, as the battery 40, a dedicated battery for the sensor module 3 may be used. However, in a case where a sensor module other than the sensor module 3 is mounted on a human body, a battery shared with the other sensor module may also be used. The power of the battery 40 is fed to the CPU 31 and the like via the connectors 45, 32. Thereby, it is possible to measure $SPO_2$ with the sensor module 3.

In this way, in the sensor module 3, the antenna 35 is arranged at the position at which it overlaps the coupling part 23 of the holding member 2, as seen from above, and does not overlap the other electronic components 30, as seen from above. Thereby, it is possible to secure predetermined distances or longer between the antenna 35 and the measurement target and other electronic components 30. As a result, the antenna 35 can exhibit stable communication performance.

In the meantime, in the case where the measurement target is a finger, it is not possible to implement stable communication performance if the antenna 35 is bought close to the finger, because the dielectric constant of the finger is high, such as about 40 to 70, and is different depending on persons. When the antenna 35 and the finger are separated by 2 mm or longer, it is possible to reduce an influence of the finger, so that the antenna 35 can exhibit stable communication performance. For this reason, when the sensor module 3 is mounted to the fingertip 500 of the test subject, the antenna 35 is preferably arranged at the most distal end-side of the fingertip 500 of the test subject of the electronic components 30.

Also, in the sensor module 3, the dielectric constant of the holding member 2 is preferably 1 to 5. Thereby, since the holding member 2 of which the dielectric constant (about 1 to 5) is sufficiently lower than the dielectric constant (about 40 to 70) of the finger is arranged in the vicinity of the antenna 35, the antenna 35 can exhibit more stable communication performance.

Also, the holding member 2 has a predetermined thickness (for example, 4 mm) so as to separate the antenna 35 and the finger each other. Thereby, the sensor module 3 can be made to be robust against a shock from the outside.

Also, in the semiconductor device 1 of the sensor module 3, the electronic components 30 are mounted in a high density on the wiring substrate 10 of a multi-layered structure having fine patterns. For this reason, even when the electronic component including the light-emitting unit, the light-receiving unit and the control circuit and to be used for measurement are mounted on one wiring substrate 10, it is possible to make the sensor module 3 small. Also, in the semiconductor device 1 of the sensor module 3, the component mounting parts M and the component non-mounting parts N are alternately arranged. For this reason, it is possible to easily deform the semiconductor device 1 by bending the component non-mounting parts N.

First Modified Example of First Exemplary Embodiment

In a first modified example of the first exemplary embodiment, an example of the wiring substrate and the holding member having different shapes from the first exemplary embodiment is described. Meanwhile, in the first modified example of the first exemplary embodiment, the descriptions of the same constitutional components as the first exemplary embodiment may be omitted.

Figure 7:
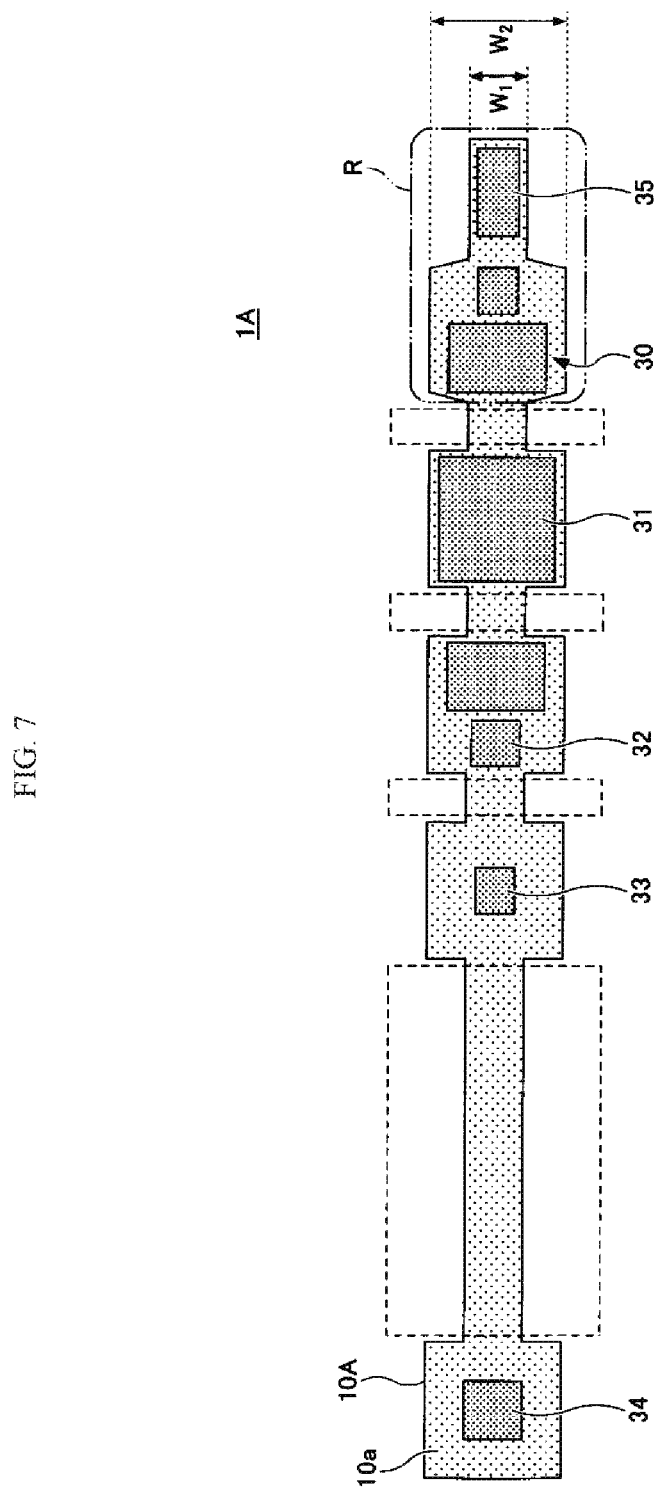
FIG. 7 is a plan view exemplifying a semiconductor device in accordance with a first modified example of the first exemplary embodiment.

FIG. 7 is a plan view exemplifying a semiconductor device in accordance with the first modified example of the first exemplary embodiment. A sectional view exemplifying the semiconductor device in accordance with the first modified example of the first exemplary embodiment is not shown because it is similar to FIG. 2B. FIG. 7 depicts a state before a semiconductor device 1A is assembled (bent) as a part of the sensor module 3.

Referring to FIG. 7, the semiconductor device 1A includes a wiring substrate 10A and the electronic components 30. In a region R at one end-side of the semiconductor device 1A, a width W1 of a region in which the antenna 35 of the wiring substrate 10A is mounted is narrower than a width W2 of regions in which the other electronic components 30 are mounted.

Figure 8:
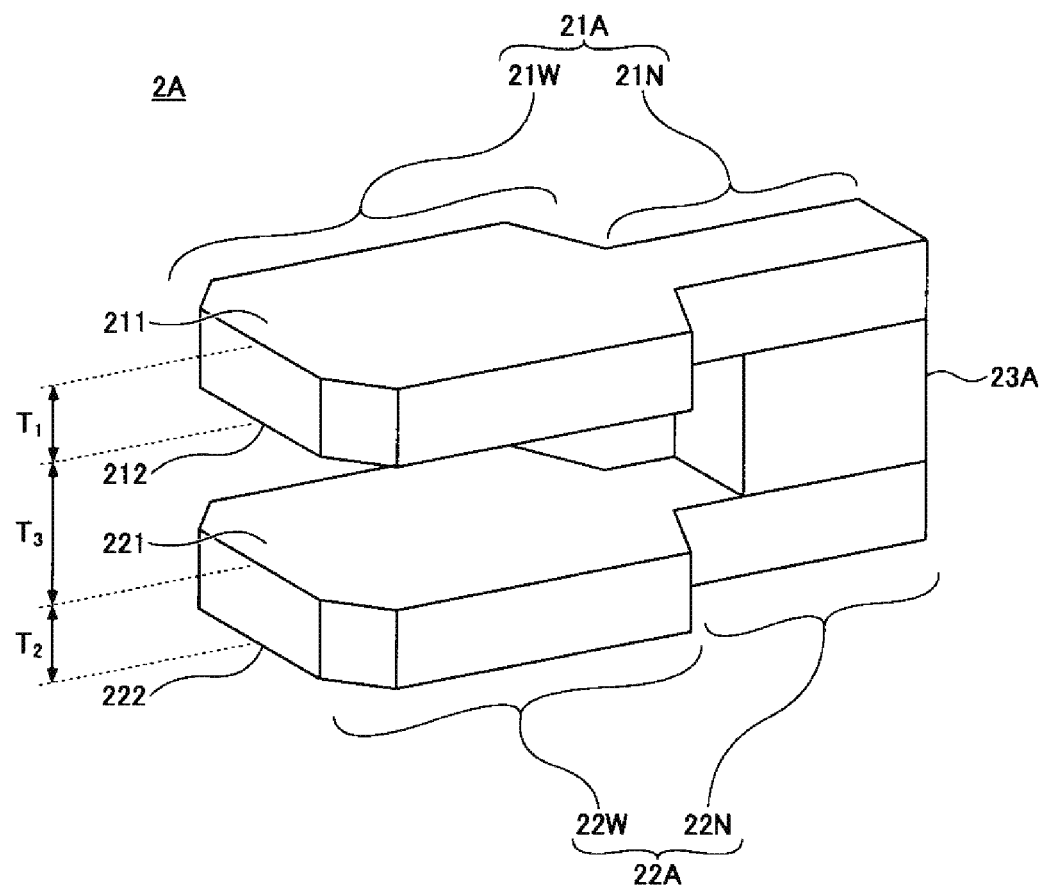
FIG. 8 is a perspective view exemplifying a holding member in accordance with the first modified example of the first exemplary embodiment.

FIG. 8 is a perspective view exemplifying a holding member in accordance with the first modified example of the first exemplary embodiment. Referring to FIG. 8, a holding member 2A includes a first plate-shaped part 21A, a second plate-shaped part 22A, and a coupling part 23A, and can hold a part of the semiconductor device 1A. The holding member 2A may be formed into a U-shape, for example, as seen from a side, by the first plate-shaped part 21A, the second plate-shaped part 22A and the coupling part 23A.

The first plate-shaped part 21A has a wide width part 21W at a side facing the second plate-shaped part 22A, and a narrow width part 21N, which has a width narrower than the wide width part 21W, at a side of the wide width part 21W facing toward the coupling part 23A. Also, the second plate-shaped part 22A has a wide width part 22W at a side facing the first plate-shaped part 21A, and a narrow width part 22N, which has a width narrower than the wide width part 22W, at a side of the wide width part 22W facing toward the coupling part 23A. Also, the width of the narrow width part 21N of the first plate-shaped part 21A, the width of the narrow width part 22N of the second plate-shaped part 22A, and a width of the coupling part 23A are substantially the same.

The planar shapes of the first plate-shaped part 21A and the second plate-shaped part 22A are similar to (substantially the same as) the planar shape of the region R of the semiconductor device 1A. Thereby, when fixing the semiconductor device 1A to the holding member 2A, in the same manner as FIG. 1, it is possible to easily position the region R of the semiconductor device 1A with respect to the first surface 211 of the first plate-shaped part 21A. In this case, the region in which the antenna 35 of the wiring substrate 10A is mounted is located in a region, which overlaps the coupling part 23A as seen from above, on the narrow width part 21N of the first plate-shaped part 21A.

Also, the widths of the first plate-shaped part 21A and the second plate-shaped part 22A are partially reduced, so that the holding member 2A can be made lighter than the holding member 2 (refer to FIG. 4).

Second Modified Example of First Exemplary Embodiment

In a second modified example of the first exemplary embodiment, an example of the holding member having a different shape from the first exemplary embodiment is described. Meanwhile, in the second modified example of the first exemplary embodiment, the descriptions of the same constitutional components as the first exemplary embodiment may be omitted.

Figure 9:
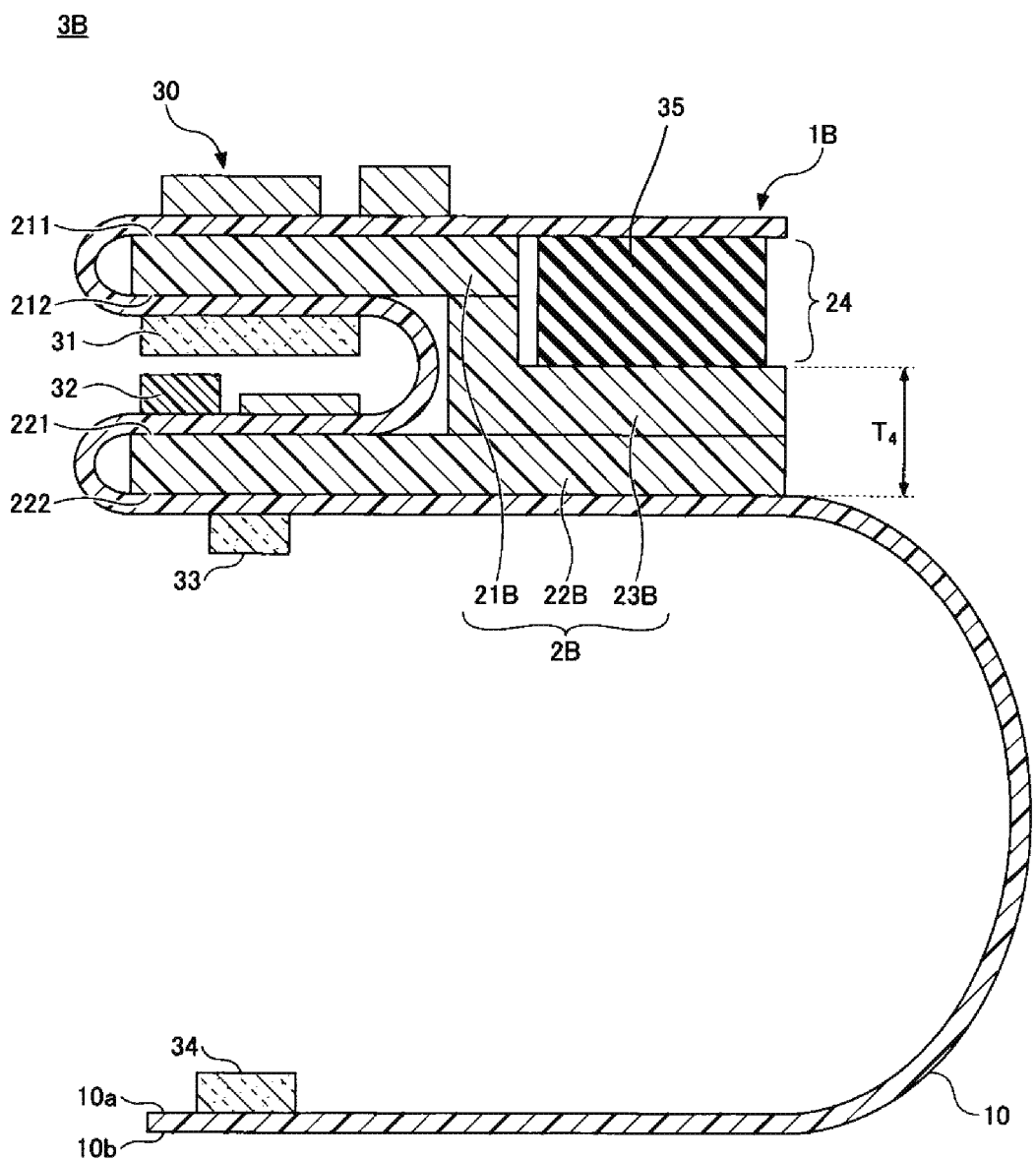
FIG. 9 is a sectional view exemplifying a sensor module in accordance with a second modified example of the first exemplary embodiment.

FIG. 9 is a sectional view exemplifying a sensor module in accordance with the second modified example of the first exemplary embodiment. As shown in FIG. 9, a sensor module 3B includes a semiconductor device 1B and a holding member 2B.

In the semiconductor device 1B, the antenna 35 is mounted on the other surface 10b of the wiring substrate 10 (a surface facing toward a step part 24, which will be described later). That is, in the semiconductor device 1B, the antenna 35 is mounted on a surface of the wiring substrate 10, which is opposite to one surface 10a on which the other electronic components 30 are mounted.

In the holding member 2B, the first plate-shaped part 21B is smaller than the second plate-shaped part 22B, as seen from above. The coupling part 23B has an L-shape, as seen from a side, and has a region that does not overlap the first plate-shaped part 21B, as seen from above. In the region where the first plate-shaped part 21B and the coupling part 23B do not overlap, as seen from above, the holding member 2B has the step part 24 sunk from the first surface 211 of the first plate-shaped part 21B toward the third surface 221 of the second plate-shaped part 22B.

A surface of the antenna 35 facing toward the wiring substrate 10 is flush with or lower than the first surface 211 of the first plate-shaped part 21B. A surface of the antenna 35 opposite to the wiring substrate 10 may be in contact with the coupling part 23B. The surface of the antenna 35 opposite to the wiring substrate 10 may be bonded to the coupling part 23B by an acryl-based adhesive, for example. In this way, the antenna 35 is arranged on the coupling part 23B so as not to protrude from the step part 24. Thereby, it is possible to make a height of the sensor module 3B lower than the sensor module 3 (refer to FIG. 1).

Even though the height of the sensor module 3B is made lower, a thickness $T_4$ of the holding member 2B below the antenna 35 is set to 2 mm or greater, so that when the sensor module 3B is mounted to the finger, it is possible to reduce the influence of the finger. As a result, the antenna 35 can exhibit stable communication performance.

In the meantime, the antenna 35 may be mounted on one surface 10a of the wiring substrate 10, the wiring substrate 10 may be bent from the first surface 211 of the first plate-shaped part 21B along an inner surface and an inner bottom surface of the coupling part 23B, and the antenna 35 may be arranged on the coupling part 23B so as not to protrude from the step part 24.

Third Modified Example of First Exemplary Embodiment

In a third modified example of the first exemplary embodiment, an example where the sensor module has a reinforcement member is described. Meanwhile, in the third modified example of the first exemplary embodiment, the descriptions of the same constitutional components as the first exemplary embodiment may be omitted.

Figure 10:
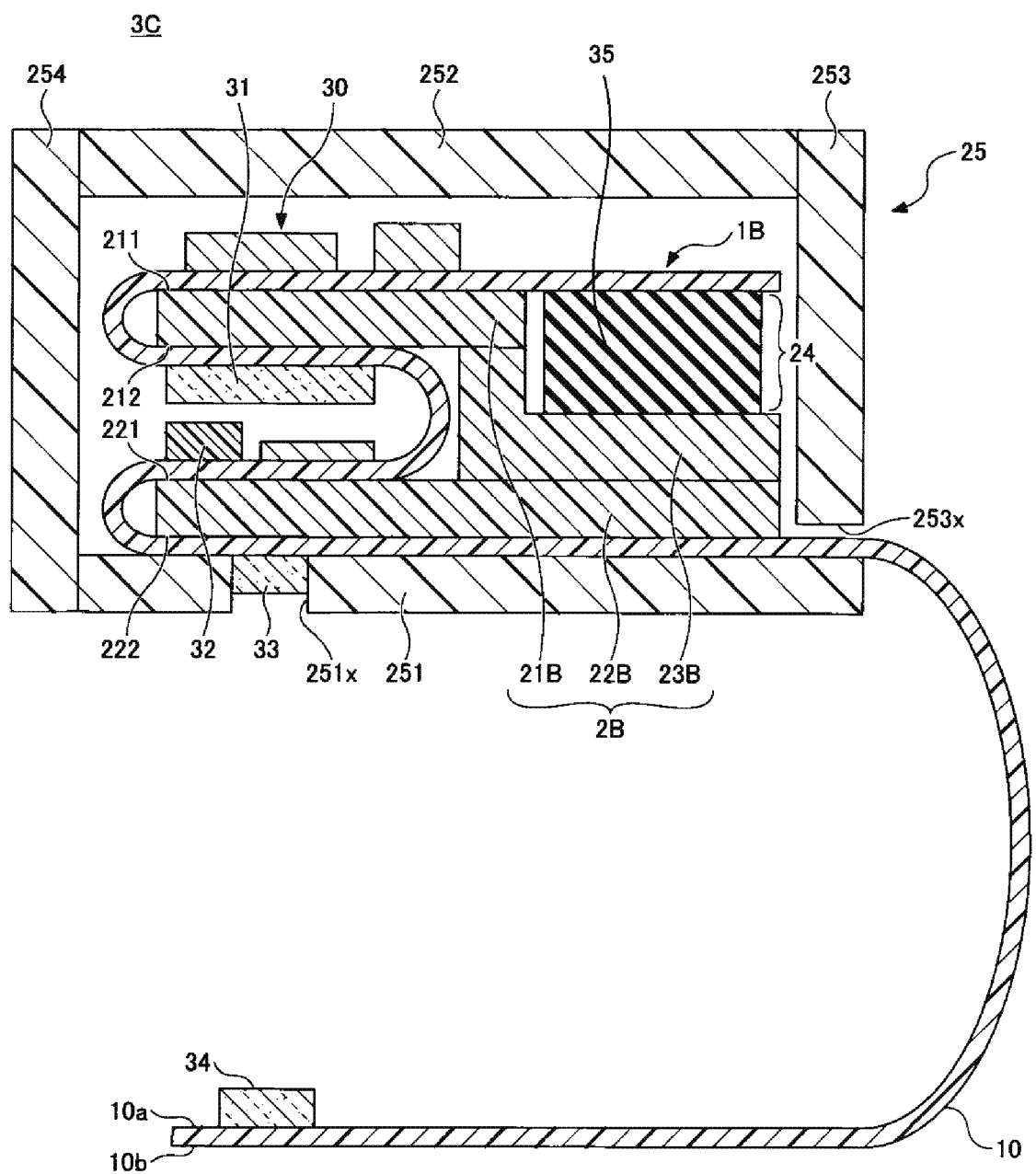
FIG. 10 is a sectional view exemplifying a sensor module in accordance with a third modified example of the first exemplary embodiment.

FIG. 10 is a sectional view exemplifying a sensor module in accordance with the third modified example of the first exemplary embodiment. As shown in FIG. 10, a sensor module 3C is different from the sensor module 3B (refer to FIG. 9), in that it includes a reinforcement member 25.

The reinforcement member 25 has a box shape so that the semiconductor device 1B and the holding member 2B are to be accommodated therein. The reinforcement member 25 may be formed by bonding a bottom plate part 251, a top plate part 252, and side plate parts 253, 254 with the semiconductor device 1B and the holding member 2B being accommodated therein, for example. In this case, the LED 33 is exposed into a through-hole 251x formed in the bottom plate part 251. Also, the other end-side of the semiconductor device 1 extends from a through-hole 253x formed in the side plate part 253 to an outside of the reinforcement member 25.

The bottom plate part 251, the top plate part 252, and the side plate parts 253, 254 may be formed of acryl, for example. For bonding of the bottom plate part 251, the top plate part 252 and the side plate parts 253, 254, an acryl-based adhesive may be used, for example. Alternatively, acryl screws may be used for the bonding. In this case, the bottom plate part 251, the top plate part 252 and the side plate parts 253, 254 can be easily disassembled.

In this way, the reinforcement member 25 configured to accommodate therein the semiconductor device 1B and the holding member 2B is added, so that it is possible to improve strength of the sensor module 3C. However, the reinforcement member is not necessarily required to entirely surround the semiconductor device 1B and the holding member 2B. For example, only the bottom plate part 251 having the through-hole 251x formed therein may be configured as the reinforcement member. That is, the reinforcement member may be provided only at a position at which it faces the fourth surface 222 of the second plate-shaped part 22B via the semiconductor device 1B. Thereby, it is possible to prevent the LED 33 from directly contacting the finger and to reinforce the LED 33.

The foregoing description of the exemplary embodiments of the present disclosure has been provided for the purposes of illustration and description. It is not intended to be exhaustive or to limit the present disclosure to the precise forms disclosed. Obviously, many modifications and variations will be apparent to practitioners skilled in the art. The embodiments were chosen and described in order to best explain the principles of the present disclosure and its practical applications, thereby enabling others skilled in the art to understand the present disclosure for various embodiments and with the various modifications as are suited to the particular use contemplated. It is intended that the scope of the present disclosure be defined by the following claims and their equivalents.

What is claimed is:

1. A sensor module comprising:
    a semiconductor device comprising a flexible wiring substrate and a plurality of electronic components mounted on the wiring substrate, the plurality of electronic components including an antenna and at least one other additional electronic component, the antenna being mounted on the wiring substrate at one end of the wiring substrate; and
    a holding member configured to hold a part of the semiconductor device, the holding member comprises:
    a first plate-shaped part having a first surface and a second surface, the second surface being an opposite surface to the first surface,
    a second plate-shaped part having a third surface and a fourth surface, the fourth surface being an opposite surface to the third surface, and
    a coupling part configured to couple the first plate-shaped part and the second plate-shaped part to each other so that the second surface and the third surface have parts facing each other with a space therebetween,
    wherein the one end of the wiring substrate is fixed to the holding member so that the antenna overlaps the coupling part, as seen from above, and the antenna does not overlap the at least one other additional electronic component of the plurality of electronic components, as seen from above,
    wherein a part of the wiring substrate continuing to the one end of the wiring substrate is folded back so as to be arranged sequentially along the first surface, the second surface, the third surface, and the fourth surface, and
    wherein the other end of the wiring substrate extends in an elastically deformable state from the fourth surface.

2. The sensor module according to claim 1, wherein the sensor module is configured to be mounted to a fingertip of a test subject so that when the holding member is arranged at a nail-side of the fingertip of the test subject, the antenna is arranged at a most distal end-side of the fingertip of the test subject among the plurality of electronic components.

3. The sensor module according to claim 1, wherein a component mounting part in which the plurality of electronic components are mounted on the wiring substrate and a component non-mounting part in which the plurality of electronic components are not mounted on the wiring substrate are alternately arranged in a longitudinal direction of the semiconductor device, and wherein the folded-back part of the semiconductor device is the component non-mounting part.

4. The sensor module according to claim 1, wherein a dielectric constant of the holding member is 1 to 5.

5. The sensor module according to claim 1, wherein the first plate-shaped part has a wide width part at a side facing the second plate-shaped part, and a narrow width part, which has a width narrower than the wide width part, at a side of the wide width part facing toward the coupling part,
    wherein a width of a region of the wiring substrate, in which the antenna is mounted, is narrower than a region in which the at least one other additional electronic component of the plurality of electronic components is mounted, and
    wherein the region in which the antenna is mounted is located on the narrow width part.

6. The sensor module according to claim 1, wherein the coupling part has a region that does not overlap the first plate-shaped part, as seen from above,
    wherein in the region, the holding member has a step part sunk from the first surface of the first plate-shaped part toward the third surface of the second plate-shaped part, and
    wherein the antenna is arranged on the coupling part so as not to protrude from the step part.

7. The sensor module according to claim 6, wherein the antenna is mounted on a surface of the wiring substrate facing toward the step part.

8. The sensor module according to claim 1, wherein a reinforcement member is provided at a position at which it faces the fourth surface of the second plate-shaped part.

9. The sensor module according to claim 1, wherein the at least one other additional electronic component of the plurality of electronic components comprises a light-emitting element and a light-receiving element, and
    wherein in the semiconductor device, one of the light-emitting element and the light-receiving element is mounted in a region arranged in the fourth surface, and the other of the light-emitting element and the light-receiving element is mounted in a region extending from the fourth surface.

10. The sensor module according to claim 9, wherein the sensor module is configured to be mounted to a fingertip of a test subject so that, by arranging the holding member at a nail-side of the fingertip of the test subject and inflecting the region extending from the fourth surface from the nail-side of the fingertip of the test subject toward a bulging part-side, the light-emitting element and the light-receiving element can be arranged to face each other with the fingertip being interposed therebetween.

* * * * *